United States Patent [19]

Tidwell

[11] Patent Number: 5,540,692
[45] Date of Patent: Jul. 30, 1996

[54] REPLICATOR FOR RESECTING BONE TO MATCH A PATTERN

[75] Inventor: Durrell G. Tidwell, Burleson, Tex.

[73] Assignee: Midas Rex Pneumatic Tools, Inc., Fort Worth, Tex.

[21] Appl. No.: 274,998

[22] Filed: Jul. 13, 1994

[51] Int. Cl.$^6$ ................................................. A61B 17/00
[52] U.S. Cl. ................................ 606/79; 606/87; 606/86
[58] Field of Search .................................. 606/80, 79, 87, 606/88, 89, 96, 102, 86, 167, 170, 180; 409/64, 79, 80, 84, 85, 87, 88, 93, 125

[56] References Cited

U.S. PATENT DOCUMENTS

| | | | |
|---|---|---|---|
| 4,183,284 | 1/1980 | Laskowski | 409/89 |
| 4,643,622 | 2/1987 | Winski | 409/84 |
| 5,007,912 | 4/1991 | Albrektsson et al. | 606/87 |
| 5,057,112 | 10/1991 | Sherman et al. | 606/79 |
| 5,086,401 | 2/1992 | Glassman et al. | 606/53 X |
| 5,112,336 | 5/1992 | Krevolin et al. | 606/96 |
| 5,190,547 | 3/1993 | Barber, Jr. et al. | 606/79 |

*Primary Examiner*—Guy Tucker
*Attorney, Agent, or Firm*—James E. Bradley; Mark W. Handley

[57] ABSTRACT

A replicator is provided for precisely resecting bone into a desired shape of a pattern. A pattern holder and a bone holder are spaced apart from each other, and rotatably mounted to a cylindrical shaft for indexing through corresponding predetermined angular increments about two parallel axes, which are perpendicular to an axis of the cylindrical shaft. A linkage means connects a probe and cutting tool to a frame for allowing free movement of the probe and cutting tool with respect to the frame, in three dimensions, while maintaining end tips of the probe and cutting tool parallel to the axis of the shaft. The probe and cutting tool are moved to trace the tip of the probe over an exterior surface of the pattern while operating the cutting tool to cut contours of the pattern into the bone. The pattern and bone holders may be rotated with the cylindrical shaft about the axis of the cylindrical shaft. The pattern and bone holders are rotated through the corresponding angular increments about the two parallel axes and are rotated together about the axis of the cylindrical shaft, for presenting the pattern and bone to the probe and cutting tool for different angles of approach.

19 Claims, 4 Drawing Sheets

REPLICATOR FOR RESECTING BONE TO MATCH A PATTERN

BACKGROUND OF THE INVENTION

1. Field of the Invention

This invention relates in general to equipment for resecting bones during implant and prosthetic surgery so as to match a pattern.

2. Description of the Prior Art

During certain types of orthopedic surgery, there is a need to cut or resect away part of the bone to a desired shape. For example, in the case of grafting a donor bone section to replace a diseased bone section, portions of the donor bone joint must be shaped to resemble the diseased bone joint as much as possible. As another example, a tibial plateau prosthesis may be implanted in the leg of a user while retaining an existing femur. In that case, the existing femur must be resected to match the tibial plateau of the prosthesis as much as possible. In the prior art, this may be handled using high speed bone cutting or resecting equipment. A surgeon primarily relies on a visual comparison and skillful use of the equipment. The surgeon may also make molds to assist in performing the resection.

One means for resecting bone into a particular shape is disclosed by U.S. Pat. No. 5,190,547, issued on Mar. 2, 1993 to Forest C. Barber, Jr. and Durrell G. Tidwell, which is hereby incorporated by reference as if fully set forth herein. A replicator is disclosed for resecting bone to match a desired pattern. The replicator includes a frame with a pattern holder and a bone holder. A tool holder mounts to the frame by means of a four bar linkage assembly. A cutting tool and a probe are mounted to the tool holder. The four bar linkage allows three-dimensional movement of the tool holder, but constrains the tool holder to always be in parallel with a line extending through the pattern holder and a bone holder.

The pattern holder and tool holder of the replicator of the '547 patent are adjustable for repositioning a pattern and a bone for presentation to the probe and the cutting tool for different angles of approach. However, the pattern holder and the tool holder must be realigned to correctly align the pattern and the bone for presentation to the probe and cutting tool each time the positions are adjusted. Realignment primarily relies on visual comparison for determining proper alignment between the bone holder and pattern holder in a second position.

SUMMARY OF THE INVENTION

A replicator is provided for precisely resecting bone into a desired shape of a pattern. The replicator includes a frame having a tool holder, a pattern holder and a bone holder. A probe and cutting tool are secured to the tool holder, and have tips which define a tool axis. A linkage means connects the tool holder to the frame and allows free movement of the tool holder in three dimensions, while maintaining the tool axis in parallel to previous positions. The tool holder is moved in the three dimensions to trace a tip of the probe over an exterior surface of the pattern while operating the cutting tool to cut contours of the pattern into the bone.

The pattern holder and bone holder are spaced apart and rotatably mounted about two parallel axes. Indexing means provide predetermined angular increments through which the pattern holder and bone holder may be rotated through corresponding angular increments about the two parallel axes for presenting to the probe and cutting tool for different angles of approach. The pattern holder and the bone holder are also mounted to a cylindrical shaft having an axis which is perpendicular to the two parallel axes. The pattern holder and the bone holder may be rotated with the cylindrical shaft about the axis of the cylindrical shaft for presenting the pattern and bone to the probe and cutting tool for different angles of approach.

DETAILED DESCRIPTION OF THE INVENTION

Figure 1:
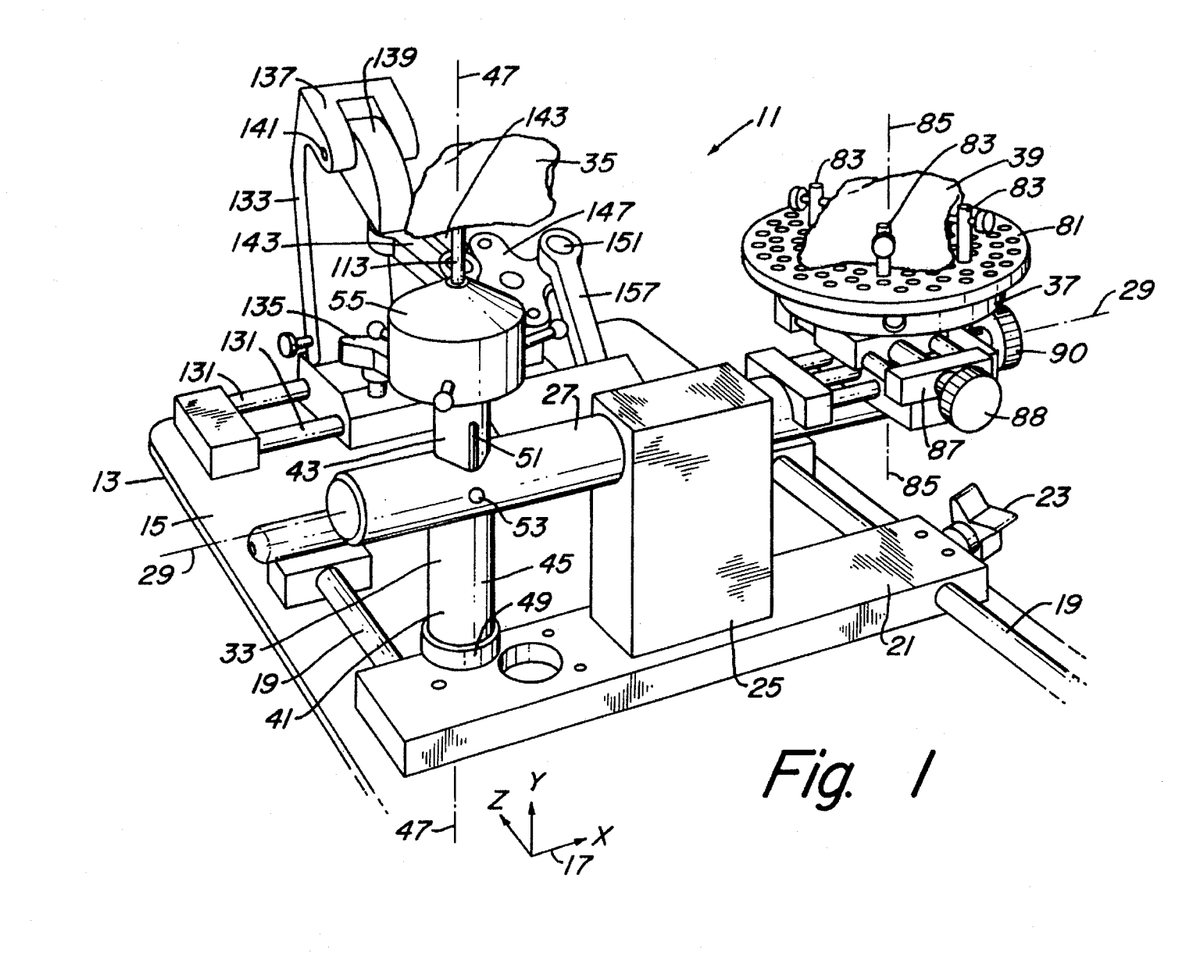
FIG. 1 is a perspective view depicting a replicator apparatus constructed in accordance with this invention, with the replicator depicted in a first position.

Referring to FIG. 1, replicator 11 is constructed to be utilized in an operating room during surgery. Replicator 11 has a frame 13 that includes a base plate 15. Base plate 15 will rest on a table in the operating room, and defines an X-axis 17, a Y-axis, and a Z-axis. A pair of slides 19, which are smooth, cylindrical bars, are mounted to base plate 15. Slides 19 are oriented along a Z-axis. A platform 21 mounts slidably to slides 19. A knob 23 controls a set screw for securing platform 21 in a desired position relative to base plate 15.

Specimen post 25 mounts to platform 21 for slidably securing post 25 with respect to base plate 15. Cylindrical shaft 27 extends through post 25, having shaft axis 27 which extends parallel to X-axis 17. Cylindrical shaft 27 is rotatably supported within specimen post 25 for rotating about shaft axis 29 into selected positions. Cylindrical shaft 27 is held in a selected position by a securing means, which in the preferred embodiment is a ball and socket indexing means, such as indexing means 57 and 59 discussed below in reference to FIG. 3. In other embodiments of the present invention, other types of securing means may be used, such as a set screw similar to the set screw used in combination with knob 23 to secure platform 21 with respect to slides 19.

Pattern support member 33 is mounted to cylindrical shaft 27 to secure pattern 35 to cylindrical shaft 27 for rotating about shaft axis 29 with cylindrical shaft 27. In the preferred embodiment, pattern 25 will be a mold formed by the surgeon during surgery. Pattern support member 33 includes pattern post 41. Pattern post 41 is of a telescoping type, having an upper section 43 which telescopes upward from lower section 45 in along pattern axis 47, which is perpendicular to shaft axis 29. An adjusting knob 49 is turned to adjust the overall length of pattern post 41. Groove 51 provides a slot in upper section 43 into which screw 53 extends to prevent upper section 45 from rotating about pattern axis 47. Stem support 55 is rotatably mounted to upper section 43 for rotating about pattern axis 47.

Figure 3:
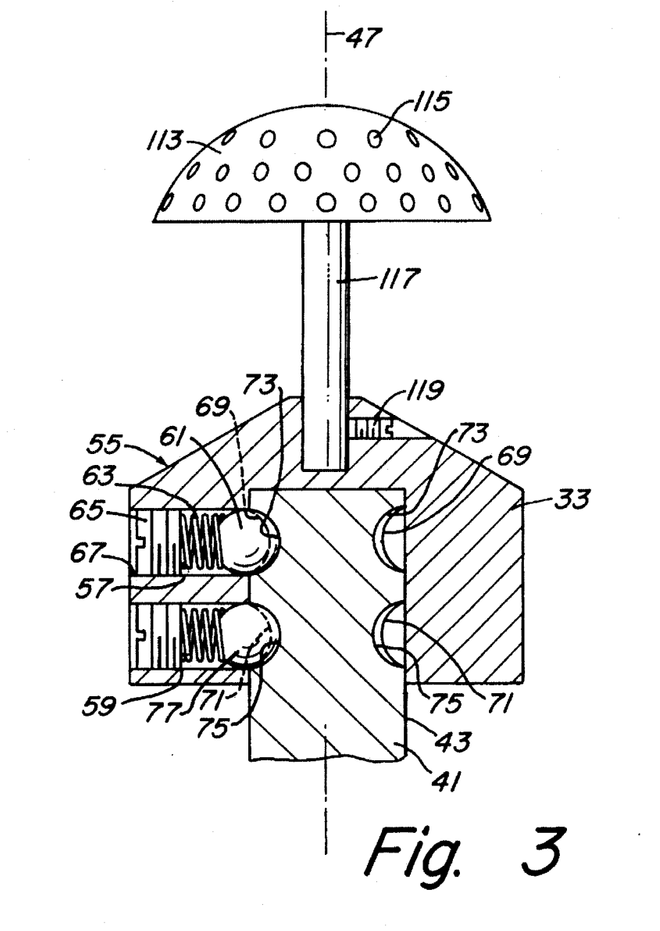
FIG. 3 is a sectional view depicting the pattern holder rotatably mounted to a post, and detent assemblies for selectively rotating the pattern holder through predetermined angular displacements.

Referring to FIG. 3, a partial section view depicts stem support 55 and upper section 43 of pattern post 41. Indexing means 57 and 59 define predetermined angular increments about which stem support 55 may be rotated about pattern axis 47. Two indexing means, 57 and 59, are used in the preferred embodiment to reduce the wobble of stem support 55 with respect to pattern post 41.

In the preferred embodiment, indexing means 57 and 59 each include identical detent assemblies, with indexing means 57 having a ball 61, a spring 63 and a set screw 65 within hole 67. Two parallel grooves 69, 71 extend circumferentially around the exterior of upper section 43. Six detents 73, or recesses, are spaced apart 60 degrees about pattern axis 47, into the bottom of groove 69 for receipt of balls 61. Six more detents 75 extend into the bottom of groove 71 for receipt of ball 77. When balls 61 and 77 are not engaged in one of detents 73 or 75, respectively, they remain engaged within either of grooves 69, 71 to prevent removal of stem support 55 from upper section 43.

A pattern holder 113 mounts to pattern support member 33. Pattern holder 113 has a plurality of holes 115 on its face to enhance the adherence of a clay-like mold placed thereon to provide pattern 35. Pattern holder 113 is a disk, slightly convex on its face. Pattern holder 113 is mounted to a stem 117 that extends into stem support 55. An adjusting screw 119 will secure stem 117 in a desired position.

Referring to FIG. 1, bone support member 37 is mounted to cylindrical shaft 27, spaced apart from pattern support member 33. Bone support member 37 secures bone 39 to cylindrical shaft 27. Bone support member 37 is rotatable about shaft axis 29 with cylindrical shaft 27 and pattern support member 33, in a fixed relationship to pattern support member 33.

Bone support member 37 includes bone plate 81, into which a plurality of holes are formed for mounting screw clamps 83. Bone plate 81 is a circular rotatable plate. Bone plate 81 is rotatable about bone axis 85, which extends parallel to pattern axis 47. Screw clamps 83 are spaced 120 degrees apart from each other for tightening against a section of a bone 39. Bone 39 will typically be a section of a donor bone for implanting in a human body. For example, bone 39 may be a femur of a knee joint. Bone plate 81 can be rotated relative to frame 13 for preselected angular distances about axis 85 of bone support member 37.

Bone support member 37 further includes adjustment means 87 for positioning bone 39 within a plane which is defined to be perpendicular to bone axis 85 and parallel to shaft axis 29 of cylindrical shaft 27. Knob 88 may be rotated to move bone 39 in direction which is perpendicular to shaft axis 29 of cylindrical shaft 27. Knob 90 may be rotated to move bone 39 in the in direction which is parallel to shaft axis 29.

Figure 4:
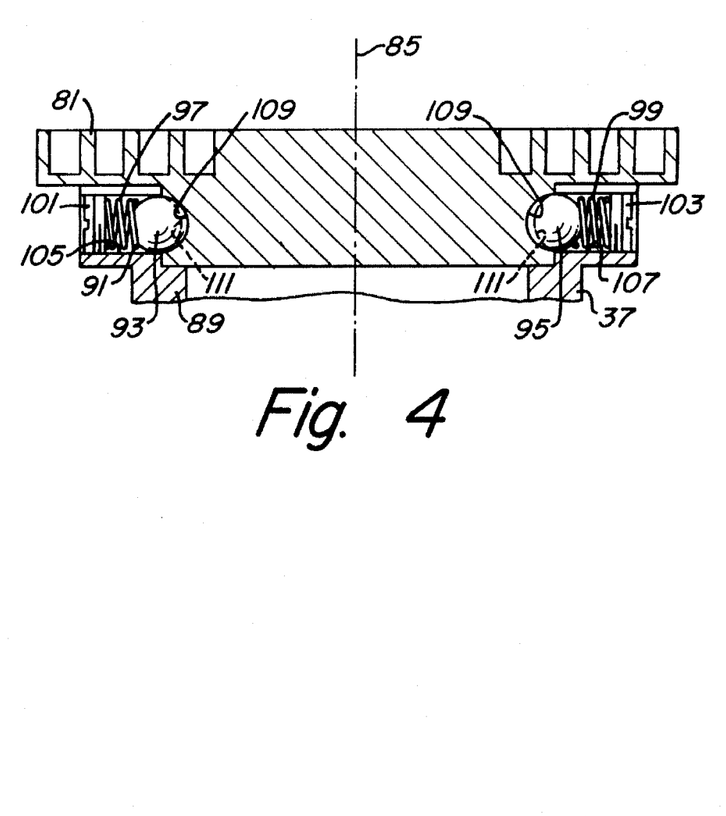
FIG. 4 is a sectional view depicting the bone holder rotatably mounted within a bracket, and a detent assembly for selectively rotating the bone holder through predetermined angular displacements.

Referring to FIG. 4, a partial section view depicts bone plate 81 in member 89. Indexing means 91 defines predetermined angular increments through which bone plate 81 may be rotated within member 89. In the preferred embodiment, indexing means 91 includes a detent assembly, which is similar to the detent assembly of indexing means 57 and 59. Indexing means 91 includes balls 93 and 95, springs 97 and 99, and set screws 101 and 103, which extend within holes 105 and 107, respectively. Groove 109 extends circumferentially around the exterior of member 89. Six detents 111, or recesses, are spaced apart 60 degrees about bone plate 81 and into the bottom of groove 109 for receipt of balls 93 and 95. When balls 93 and 95 are not engaged in one of detents 111, they remain engaged within groove 109 for preventing removal of bone plate 81 from within member 89.

Figure 5:
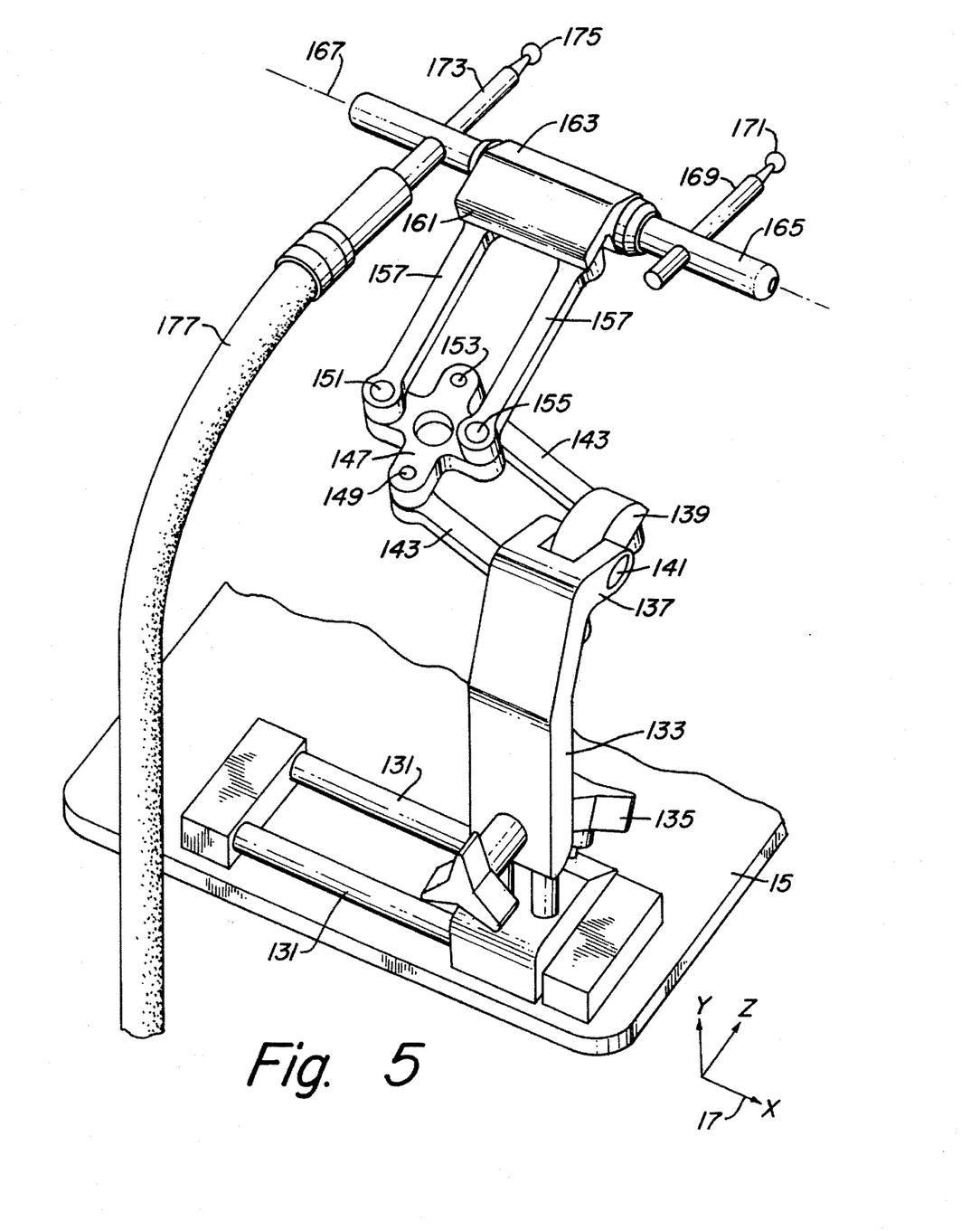
FIG. 5 is a perspective view depicting the tool holder section of the replicator of FIG. 1.

Referring to FIG. 5, a pair of slides 131 are mounted to base plate 15 perpendicular to slides 19 (shown in FIG. 1). A tool holder post 133 mounts to slides 131. An adjusting knob 135 will allow tool holder post 113 to slide and be tightened to a selected position along slides 131.

A clevis 137 is formed in the upper end of tool holder post 133. Clevis 137 includes a rotatable clevis bracket 139. Clevis bracket 139 is secured by a pin 141 to spaced apart lobes of clevis 137. Pin 141 is mounted along a clevis axis that is parallel to X-axis 17. Pin 141 allows clevis bracket 139 to swing in an y-axis and z-axis plane.

A pair of frame parallel bars 143 pivotally mount to clevis bracket 139. Frame parallel bars 143 are identical in length and size and mounted so as to always be parallel to each other. Frame parallel bars 143 each have a frame end mounted pivotally to clevis bracket 139 by spaced apart clevis bracket pivot pins 145 (not shown). Pivot pins 145 (not shown) are spaced apart from each other within the y-axis and z-axis plane. Pivot pins 145 (not shown) allow rotation of frame parallel bars 143 in a plane containing frame parallel bars 143.

The opposite ends, or plate ends, of frame parallel bars 143 connect to a linkage plate 147. Plate 147 is free floating and has four pivotal pins, referred to herein as a zero degree pin 149, a 90 degree pin 151, a 180 degree pin 153, and 270 degree pin 155. The zero degree pin 149 and the 180 degree pin 153 will always be located on a line parallel to a plane containing Z-axis 18. The 90 degree pin 151 and 270 degree pin 155 will always be located on a line parallel to X-axis 17. The frame parallel bars 143 connect to the zero degree pin 149 and 180 degree pin 153. In the embodiment shown, the ends of the frame parallel bars 143 are located on the side of plate 147 that faces frame 13.

A pair of tool holder parallel bars 157 have plate ends that connect to the 90 degree pin 151 and 270 degree pin 155. Tool holder parallel bars 157 are of identical length and are maintained always in parallel relationship to each other. The ends of tool holder parallel bars 157 are located on a side of plate 149 that faces away from frame 13.

The opposite ends of tool holder parallel bars 157 pivotally connect to tool holder pivot pins 159 (not shown) of a tool holder 161. The distance between pivot pins 159 (not shown) is the same as the distance between pivot pins 151 and 155. Similarly, this distance is the same as between pivot pins 149, 153 and pivot pin 145. Tool holder 161 includes a tool holder sleeve 163 which supports pivot pins 159. An extension member 165 extends completely through tool holder sleeve 163. Extension member 165 extends on opposite sides of sleeve 163 and is rotatable relative to sleeve 163. A tool bone axis 167 extends along extension member 165. Tool bone axis 167 is maintained by the parallel bars 143, 157 in a parallel relationship to X-axis 17 at all times.

A stylus or probe 169 mounts to one side of extension sleeve 163. Probe 169 is frictionally held in a hole extending through extension member 165. Probe 169 has a tip 171 that will trace over the contours of pattern 33 (shown in FIG. 1). Cutting tool 173 is secured in a hole provided in extension member 165 on the opposite side of sleeve 163. Cutting tool 173 is a conventional high speed pneumatic cutting instrument. Cutting tool 173 has a tip 175 that will contain a bit or other type of cutting tool for resecting the bone 39. Tip 175 is spaced apart from tip 171 the same distance as from the centerline of bone plate 81 to the centerline of pattern holder 113. Also, probe tip 171 will be positioned so that a line passing through tips 171, 175 will be parallel with axis 167 of tool holder 161 and also parallel with X-axis 17. An air hose 177 supplies air to cutting tool 173 to form the cutting action.

Figure 2:
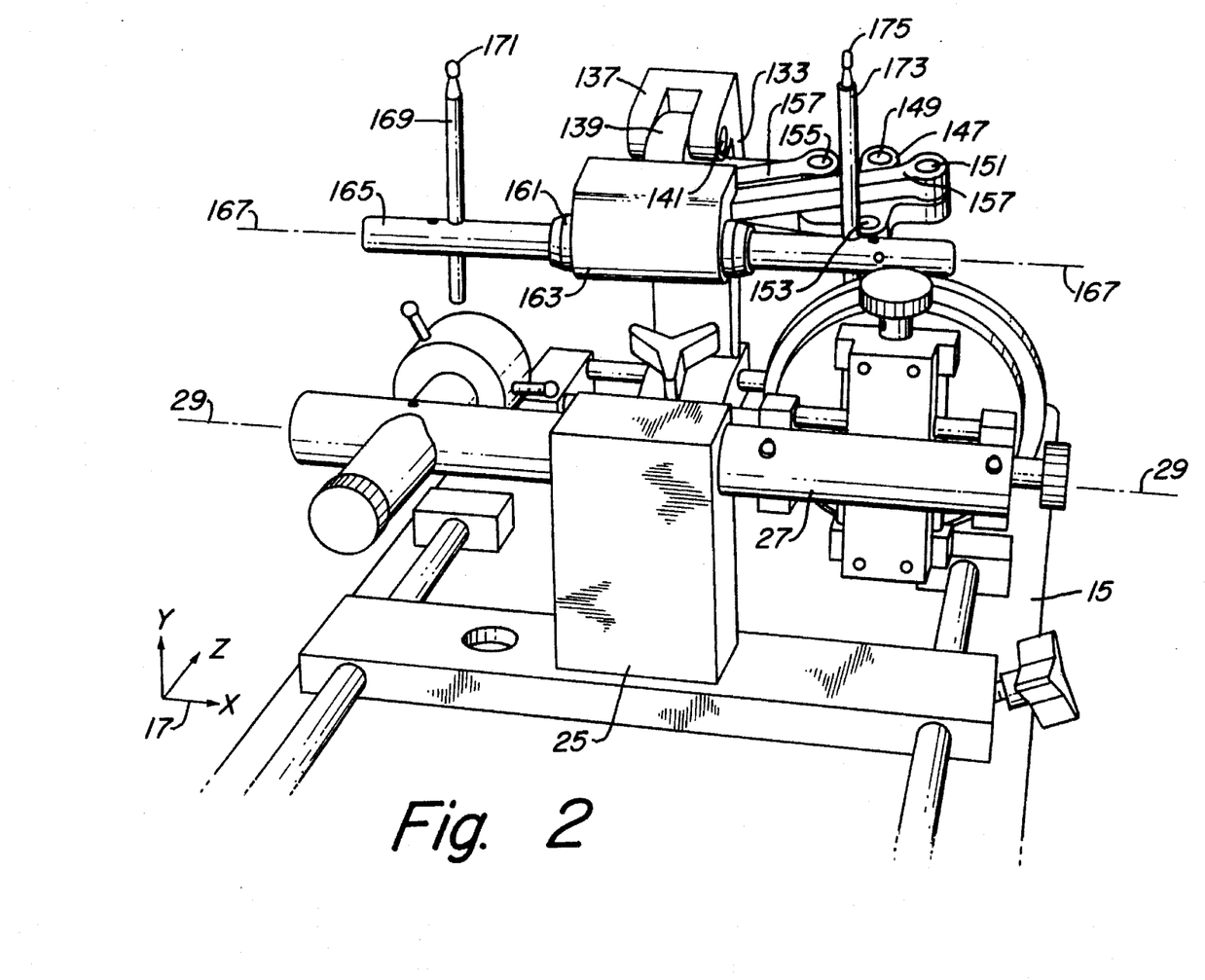
FIG. 2 is a perspective view depicting the replicator of FIG. 1 disposed in a second position.

Referring to FIGS. 1, 2 and 5, in the operation of the present invention, the surgeon will make a mold to form a pattern 35. This may be done by first cutting the diseased bone from the patient, then pressing a moldable material against the cut area in the patient using pattern holder 13. The material will harden into pattern 35, which is then placed in pattern support member 33. The surgeon takes the donor bone 39 and places it in bone support member 37.

The surgeon will adjust the adjusting knob 49 of pattern support member 33 and adjusting knobs 88 and 90 of adjustment means 87 of bone support member 37, so that centerlines of bone 39 and pattern 35, which define pattern axis 47 and bone axis 85, will be the same distance apart as the distance between cutting tool 173 and probe 169. The centerlines of bone 39 and pattern 35 are adjusted to define a bone-pattern axis that is parallel to shaft axis 29 of cylindrical shaft 27, x-axis 17, and tool bone axis 167. Adjusting knob 49 may be rotated to extend pattern 35 along pattern axis 47, which is parallel to bone axis 85 and perpendicular to shaft axis 29 of cylindrical shaft 27 and x-axis 17. Adjustment means 87 is operated by turning adjustment knob 88 to move bone 39 in a direction which is perpendicular to both bone axis 85 and shaft axis 29. Adjustment knob 90 may be turned to move bone 39 in a direction which is parallel to shaft axis 29 and x-axis 17, and perpendicular to bone axis 85.

The surgeon will align the tips 171, 175 parallel with axis 167 of tool holder 161 by using a T-shaped template (not shown). Probe tip 171 should be set to touch pattern 35 when cutting tool 173 is touching bone 39, and clevis bracket 139 will be oriented approximately parallel to z-axis 16.

The surgeon will turn on cutting tool 173 to begin resecting bone 39. The surgeon will trace probe 169 over all portions of the contours of pattern 35 while resecting the donor bone 39. The parallel bars 143, 157 will allow tool holder 161 to rotate freely in-a plane parallel to the planes containing the parallel bars 143, 157. The clevis bracket 139 will allow the tool holder 161 to rotate about clevis bracket pin 141 in y-axis directions. This provides three-dimensional movement. The parallel bars 143, 157, however, construct the tool holder 161 such that the tool holder 161 will always be parallel to the X-axis 17. This assures that the section on the bone 39 will precisely match the pattern 35.

Once a portion of the contours of a three dimensional surface of pattern 35 are replicated into bone 39, pattern 35 and bone 39 may be repositioned for presentation to probe 169 and cutting tool 173 by one of two methods. First, cylindrical shaft 27 may be rotated about shaft axis 29 such as from a first position shown in FIG. 1, to a second position shown in FIG. 2. Since the pattern axis 47 and bone axis 85 are parallel and perpendicular to shaft axis 29, they may be rotated together about shaft axis 29 with pattern 35 and bone 39 in a fixed relationship.

A second method for repositioning pattern 35 and bone 39 is to rotate pattern. 35 about pattern axis 47 and bone 39 about bone axis 85, in the same direction of rotation through predetermined angular increments. Indexing means 57 and 59 include detents 57, 59 and 91, which define equal, predetermined, angular increments through which pattern 35 and bone 39 may be selectively rotated about pattern axis 47 and bone axis 85, respectively. Thus, pattern 35 and bone 39 may be selectively rotated through equal angular increments about parallel axes, which are defined to be perpendicular to shaft axis 29, x-axis 17, tool axis 167, and the bone-pattern axis. Once completed, the surgeon will remove donor bone 39 and implant it in the patient.

The invention has a significant advantage over prior art resecting tools in that the pattern and bone may be selectively rotated through equal angular increments for presentation to the probe and cutting tool for different angles of approach. One method for rotating the pattern and bone through equal angular increments is to rotate the pattern and bone around a cylindrical shaft, which is parallel to the bone-pattern and tool axes. In the preferred embodiment, the cylindrical shaft may be rotated through predetermined angular increments defined by detents. Another method is to rotate the pattern and the bone through predetermined, equal, angular increments about mutually parallel axes, which are perpendicular to the tool axis and bone-pattern axis. Thus, the pattern and bone will remain aligned for presentation to the probe and cutting tool.

Although the invention has been described with reference to a specific embodiment, this description is not meant to be construed in a limiting sense. Various modifications of the disclosed embodiment as well as alternative embodiments of the invention will become apparent to persons skilled in the art upon reference to the description of the invention. It is therefore contemplated that the appended claims will cover any such modifications or embodiments that fall within the true scope of the invention.

I claim:

1. In an apparatus for resecting a bone into a desired three dimensional shape of a pattern, the apparatus having a frame, a bone holder to which the bone is adapted to be rigidly secured, a pattern holder to which the pattern is adapted to be rigidly secured, a tool holder, a cutting tool which is rigidly secured to the tool holder, a probe for moving along contours in the three dimensional shape of the pattern, post means for securing the bone holder and the pattern holder to the frame, tool means for securing the cutting tool and the probe to the frame, wherein moving the probe along the contours of the pattern moves the cutting tool relative to the bone for replicating the contours into the bone to define the desired three dimensional shape of the pattern in the bone, the improvement comprising:

pattern holder rotational means for rotating and latching the pattern holder in first predetermined angular increments about a pattern axis, for selectively rotating the pattern relative to the probe;

bone holder rotational means for rotating and latching the bone holder in second predetermined angular increments about a bone axis, which is parallel to the pattern axis, for selectively rotating the bone relative to the cutting tool; and  wherein the first and second predetermined angular increments are equal to each other for correspondingly rotating the pattern holder and bone holder equal angular displacements about the pattern axis and the bone axis, respectively, to select between alternate angles of approach for presenting the bone to the cutting tool, and the probe of the pattern holder.

2. The apparatus of claim 1, wherein each of the rotational means comprises:

a member having a circumferential surface into which detents extend to define the equal angular increments; and a ball and spring assembly for indexing into the detents to determine the equal angular increments about the pattern and bone axes through which the pattern holder and bone holder are rotated.

3. The apparatus of claim 1, wherein the improvement further comprises:

means for simultaneously rotating the pattern and bone axes over equal angular displacements about a common shaft axis, which is perpendicular to the pattern and bone axes, to select between the alternate angles of approach for presenting the bone to the cutting tool, and the probe to the pattern holder.

4. The apparatus of claim 1, wherein the improvement further comprises:

means for rotating the pattern and bone axes about a shaft axis, which is perpendicular to the pattern and bone axes, to select between the alternate angles of approach for presenting the bone to the cutting tool, and the probe to the pattern holder; and shaft axis indexing means having predetermined angular displacements for defining the angular displacements over which the pattern and bone axes are rotated about the shaft axis.

5. The apparatus of claim 1, wherein the improvement further comprises:

a shaft which is rotatably mounted to the frame for rotation about a shaft axis, which is perpendicular to the pattern and bone axes;

wherein the pattern holder and bone holder rotational means are rotatably mounted to the shaft perpendicular to the shaft axis; and wherein selectively rotating the shaft about the shaft axis rotates the pattern and bone axes about the shaft axis to select between the alternate angles of approach for presenting the bone to the cutting tool, and the probe to the pattern holder.

6. The apparatus of claim 1, wherein the apparatus further comprises:

a shaft which is rotatably mounted to the frame for rotation about a shaft axis, which is perpendicular to the pattern and bone axes;

wherein the pattern holder and bone holder rotational means are rotatably mounted to the shaft perpendicular to the shaft axis;

wherein selectively rotating the shaft about the shaft axis rotates the pattern and bone axes about the shaft axis to select between the alternate angles of approach for presenting the bone to the cutting tool, and the probe to the pattern holder;

detents extending into a circumferential surface of the shaft for defining angular increments over which the pattern and bone axes are equally rotated about the shaft axis; and a ball and spring assembly for indexing into the detents to determine the angular increments about the shaft axis which the pattern and bone axes are rotated.

7. In an apparatus for resecting a bone into a desired three dimensional shape of a pattern, the apparatus having a frame, a bone holder to which the bone is adapted to be rigidly secured, a pattern holder to which the pattern is adapted to be rigidly secured, a tool holder, a cutting tool which is rigidly secured to the tool holder, a probe which is rigidly secured to the tool holder for passing along contours in the desired three dimensional shape of the pattern to guide the cutting tool against the bone to define the three dimensional shape of the pattern in the bone, and wherein the tool holder is movably secured to the frame for moving the probe means and the cutting tool together along parallel paths to pass the probe means along the contours in the desired three dimensional shape of the pattern to guide the cutting tool against the bone for replicating the contours into the bone to define the desired three dimensional shape of the pattern in the bone, the apparatus comprising:

a pattern support member for rotatably mounting the pattern holder to the frame for rotation about a pattern axis, said pattern support member including a first indexing means defining first predetermined angular increments for rotating the pattern holder about the pattern axis and for maintaining the pattern holder at said first predetermined angular increments;

a bone support member for rotatably mounting the bone holder to the frame for rotation about a bone axis, which is parallel to the pattern axis, said bone support including a second indexing means defining second predetermined angular increments for rotating the bone holder about the bone axis and for maintaining the bone holder at said second predetermined angular increments; and wherein the first predetermined angular increments over which the pattern holder is rotated are the same as the second predetermined angular increments over which the bone holder is rotated, for selectively presenting the pattern to the probe and the bone to the cutting tool at corresponding angles of approach for replicating in the bone the desired three dimensional shape of the pattern.

8. The apparatus of claim 7, wherein the first and second indexing means each comprise:

detents extending into peripheries of the pattern support member and the bone support member, separated by intervals which define the predetermined angular increments; and a spring biased member for urging to extend into the detents in the peripheries of the pattern support member and the bone support member, wherein the spring biased member extends into the detents for selectively securing the bone holder and pattern holder for presenting the bone and the pattern to the cutting tool and probe, respectively, at the corresponding angles of approach for replicating the three dimensional shape of the pattern into the bone.

9. The apparatus of claim 7, further comprising:

a rotatable shaft mounted to the frame and having a shaft axis, the pattern support member and the bone support member being mounted to the shaft, with the pattern and bone axes disposed perpendicular to the shaft axis, wherein the rotatable shaft, pattern support member and probe support member are rotatable about the shaft axis for rotating the pattern and bone axes in a preselected alignment about the shaft axis.

10. The apparatus of claim 7, further comprising:

a post having a lower end secured to the frame and an upper end through which round a hole extends;

a cylindrical shaft extending through the hole in the post and rotatably secured therein for rotating about a shaft axis which is perpendicular to the pattern and bone axes;

wherein the pattern support member is mounted to the cylindrical shaft, with the pattern axis perpendicular to the shaft axis, for rotating with the shaft about the shaft axis over selectable angular displacements; and wherein the bone support member is mounted to the cylindrical shaft, with the bone axis perpendicular to the shaft axis of the cylindrical shaft, for rotating with the shaft about the shaft axis over the selectable angular displacements which the pattern support member is rotated over.

11. The apparatus of claim 7, further comprising:

the pattern support means having an adjustable length for selectively moving the pattern holder parallel to the pattern axis to adjust a position at which the pattern is disposed; and an adjustment means for selectively adjusting the position of the bone holder in two perpendicular directions within a plane which is perpendicular to the bone axis.

12. In an apparatus for resecting a bone into a desired three dimensional shape of a pattern, the apparatus having a base plate, a bone holder to which the bone is adapted to be rigidly secured, a pattern holder to which the pattern is rigidly secured, a tool holder defining a tool axis, a cutting tool which is rigidly secured to the tool holder, a probe which is rigidly secured to the tool holder for passing along contours in the desired three dimensional shape of the pattern to guide the cutting tool against the bone to define the three dimensional shape of the pattern in the bone, and wherein the tool holder is movably secured to the base plate for moving the probe means and the cutting tool together along parallel paths to pass the probe means along the contours in the desired three dimensional shape of the pattern to guide the cutting tool against the bone for replicating the contours into the bone to define the desired three dimensional shape of the pattern in the bone, the apparatus comprising:

a post having a lower end secured to the base plate and an upper end through which a hole extends;

a cylindrical shaft passing through the hole in the post and rotatably secured therein, the cylindrical shaft having a shaft axis which is parallel to the tool axis, the shaft axis extending, through the hole in the post, and wherein the cylindrical shaft is selectably rotated around the shaft axis;

a pattern support member securing the pattern holder to the cylindrical shaft and defining a pattern axis which is perpendicular to the shaft axis, the pattern support being mounted to the cylindrical shaft for rotating with the cylindrical shaft about the shaft axis over selectable angular displacements; and a bone support member securing the bone holder to the cylindrical shaft and defining a bone axis which is perpendicular to the shaft axis and parallel to the pattern axis, the bone support being mounted to the cylindrical shaft for rotating with the cylindrical shaft about the shaft axis over the selectable angular displacements, over which the pattern support member is rotated.

13. The apparatus of claim 12, further comprising:

an indexing means having preselected angular increments for defining selectable angular displacements over which the cylindrical shaft is rotated about the shaft axis.

14. The apparatus of claim 12, wherein:

the pattern support member rotatably secures the pattern holder to the cylindrical shaft, with the pattern holder being rotatable over first predetermined angular increments about the pattern axis;

the bone support member rotatably secures the bone holder to the cylindrical shaft, with the bone holder being rotatable over second predetermined angular increments about the bone axis; and the first predetermined angular increments are the same as the second predetermined angular increments.

15. The apparatus of claim 12, further comprising:

the pattern support member having an adjustable length for selectively moving the pattern holder parallel to the pattern axis to adjust a position at which the pattern is disposed from the shaft axis; and the bone support member including an adjustment means for selectively adjusting the position of the bone holder in two perpendicular directions within a plane which is perpendicular to the bone axis and parallel to the shaft axis.

16. A method for resecting bone into a desired three dimensional shape of a pattern using an apparatus the type having a frame, a cutting tool and probe secured to a tool holder having a tool axis which is moveable in three dimensions, a pattern holder and a bone holder, the method comprising the steps of:

rotatably securing the pattern holder and the bone holder to the frame for selectively rotatating through predetermined angular increments about pattern and bone axes, respectively, wherein the pattern axis is parallel to the bone axis, and wherein the predetermined angular increments through which the pattern holder is rotated about the pattern axis are equal to the predetermined angular increments through which the bone holder is rotated about the bone axis;

securing the bone to the bone holder, wherein the bone is aligned for presenting to the cutting tool for cutting the three dimensional shape therein;

securing the pattern to the pattern holder, wherein the pattern holder is align for presenting the pattern to the probe for guiding the cutting tool in replicating contours in the three dimensional shape of the pattern into the bone;

cutting contours of the three dimensional pattern into the bone from a first angle of approach of the probe with respect to the pattern and the bone with respect to the cutting tool;

rotating the pattern holder about the pattern axis for a one of the predetermined angular increments to select an angle of approach for presenting the pattern to the probe; and rotating the bone holder about the bone axis for the same one of the predetermined angular increments, to select the same angle of approach for presenting the bone to the cutting tool for replicating contours of the pattern into the bone.

17. The method of claim 16, further comprising the step of:

rotatably securing the pattern holder and the bone holder to the frame for simultaneously rotating the pattern holder and the bone holder about shaft axis which is perpendicular to the pattern and bone axes;

rotating the pattern holder about the shaft axis for a preselected angular distance to selectively present the pattern holder to the probe at a third angle of approach;

rotating the bone holder about the shaft axis for the preselected angular distance to align the bone holder with the pattern holder for presenting the bone holder to the cutting tool at the third angle of approach for replicating contours in the pattern into the bone; and cutting contours of the three dimensional pattern into the bone from the third angle of approach of the probe with respect to the pattern and the bone with respect to the cutting tool.

18. The method of claim 16, further comprising the step of:

rotatably securing the pattern holder and the bone holder to the frame for simultaneously rotating the pattern holder and the bone holder about a shaft axis which is perpendicular to the pattern and bone axes;

simultaneously rotating the pattern holder and the bone holder about the shaft axis for an angular distance to selectively present the pattern holder to the probe at a third angle of approach and to align the bone holder with the pattern holder for presenting the bone holder to the cutting tool at the third angle of approach for replicating contours in the pattern into the bone; and cutting contours of the three dimensional pattern into the bone from the third angle of approach of the probe with respect to the pattern and the bone with respect to the cutting tool.

19. The method of claim 16, further comprising the steps of;

rotatably securing the pattern holder and the bone holder to the frame for simultaneously rotating the pattern holder and the bone holder about a shaft axis which is perpendicular to the pattern and bone axes;

simultaneously rotating the pattern holder and the bone holder about the shaft axis for an angular distance to selectively present the pattern holder to the probe at a third angle of approach and to align the bone holder with the pattern holder for presenting the bone holder to the cutting tool at the third angle of approach for replicating contours in the pattern into the bone;

cutting contours of the three dimensional pattern into the bone from the third angle of approach of the probe with respect to the pattern and the bone with respect to the cutting tool;

providing an indexing means for selectively rotating the pattern holder and the bone holder about the shaft axis for predetermined angular increments which define the selected angular displacements; and wherein the selected angular displacement is selected by rotating the single shaft for a selected number of the predetermined angular increments about the shaft axis.

* * * * *